(12) United States Patent
Maier

(10) Patent No.: US 6,319,876 B1
(45) Date of Patent: *Nov. 20, 2001

(54) MICROPOROUS AMORPHOUS MIXED METAL OXIDES FOR FORM-SELECTIVE CATALYSIS

(75) Inventor: Wilhelm F. Maier, Mülheim an der Ruhr (DE)

(73) Assignee: Studiengesellschaft Kohle mbH, Mulheim an der Ruhr (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 82 days.

(21) Appl. No.: 08/913,516

(22) PCT Filed: Feb. 24, 1996

(86) PCT No.: PCT/EP96/00766

§ 371 Date: Aug. 28, 1997

§ 102(e) Date: Aug. 28, 1997

(87) PCT Pub. No.: WO96/26907

PCT Pub. Date: Sep. 6, 1996

(30) Foreign Application Priority Data

Feb. 28, 1995 (DE) .............................................. 195 06 843

(51) Int. Cl.[7] .......................... B01J 27/224; B01J 23/00; C03B 8/00; C04B 35/46

(52) U.S. Cl. .......................... 502/178; 502/350; 502/351; 502/355; 502/306; 502/326; 502/327; 502/304; 65/17.2; 501/12; 501/39

(58) Field of Search .................... 501/39, 12; 502/178, 502/350, 351, 355, 306, 307, 308, 309, 312, 314, 1, 316, 318, 319, 321, 326, 327, 330, 331, 332, 302, 333–339

(56) References Cited

U.S. PATENT DOCUMENTS

| 2,472,490 | * | 6/1949 | Plank ..................................... 501/39 |
| 3,574,583 | * | 4/1971 | Goldsmith ............................. 501/39 |
| 3,923,533 | * | 12/1975 | Hammel et al. ....................... 501/39 |
| 4,002,482 | * | 1/1977 | Coenen ................................. 501/33 |
| 4,113,660 | * | 9/1978 | Abe et al. ............................. 502/340 |
| 4,176,089 | * | 11/1979 | Cull ..................................... 502/236 |
| 4,233,169 | * | 11/1980 | Beall et al. ............................ 501/39 |
| 4,665,039 | * | 5/1987 | Kokubu et al. ........................ 501/39 |
| 4,713,338 | * | 12/1987 | Gonzalez Oliver et al. .......... 501/39 |
| 4,765,818 | * | 8/1988 | Che et al. ............................... 65/395 |
| 4,778,777 | * | 10/1988 | Eguchi et al. ......................... 501/39 |
| 5,556,689 | * | 9/1996 | Kratel et al. ........................... 501/39 |
| 5,693,134 | * | 12/1997 | Stephens ............................... 106/415 |

FOREIGN PATENT DOCUMENTS

590714 * 4/1994 (EP) .
0 590 714   4/1994 (EP) .

OTHER PUBLICATIONS

M. W. Schafer et al., "The Chemistry of and Physics with Porous Sol–Gel Glasses." Journal of Applied Physics, vol. 61, No. 12, Jun. 15 1987, New York.*

(List continued on next page.)

Primary Examiner—Mark L. Bell
Assistant Examiner—Patricia L. Hailey
(74) Attorney, Agent, or Firm—Norris McLaughlin & Marcus

(57) ABSTRACT

The invention relates to the catalytic activity and selectivity of microporous, amorphous glasses of mixed metal oxides and the application thereof in the form of shape selective, heterogeneous catalysts. Microporous, amorphous mixed metal oxides (glasses) can be formed by polycondensation of soluble metal compounds. These new materials show a temperature stability up to 800° C. These amorphous glasses shown in heterocatalytic reactions selective oxidation, hydrogenation, hydrocracking and condensation catalysis.

9 Claims, 3 Drawing Sheets

OTHER PUBLICATIONS

M. A. Cauqui et al., "Application of the Sol Gel Methods to Catalyst Preparation." Journal of Non–Crystalline Solids, vol. 147/148, No. 1, Oct. 1992.*

Chemical Abstracts, vol. 104, No. 24, Jun. 16, 1986, Abstract No. 211888.*

Chemical Abstracts, vol. 115, No. 4, Jul. 29, 1991, Abstract No. 34181t.*

M. Schaefer et al., J. Applied Physics, 61:5438–5446(1987), Jun. 1987.

M.Cauqui et al., J. Non–Crystalline Solids, 147/148:724–738(1992), Oct. 1982.

Chemical Abstract, 104:211888z (1986) Jun. 1986.

Chemical Abstract, 115:34181t(1990) Jul. 1991.

* cited by examiner

MICROPOROUS AMORPHOUS MIXED METAL OXIDES FOR FORM-SELECTIVE CATALYSIS

The catalytical selectivity has been developed to an increasingly important touchstone for technical applications of new heterogeneous catalysts, in spite of the great technical progress in the heterogeneous catalysis. The limits of the technical selectivity of the present catalyst generation most probably have been reached in all of the important chemical manufacturing processes. Highly developed chemical reaction techniques and improvements of the catalysts by semi-empirical catalyst modification by means of additives, surface modification and optimization of the pore structure are state of the art in the development of chemical processes. Shape selectivity, a first step for substrate selectivity, is the base of success of the zeolites, which constitute the most important new generation of heterogeneous catalysts. Shape selectivity is understood to denote selectivity of the formation of a chemical product; such selectivity is due to the differently limited mobilities of the various product molecules in the pores of the catalyst. It is prerequisite that the diameter of the pores of the catalyst is only slightly larger than that of the product molecules. Thus, the formation of p-xylene will be achieved, for instance, by isomerization of xylene mixtures by means of the acidic H-ZSM-5 zeolites, since the p-xylene, due to its straight form, is capable of diffusing considerably faster in the narrow pore channels of the zeolite, than are the more bulky o-xylene and m-xylene (D. H. Olsen, W. O. Haag, ACS Symp. Ser. 248 (1984) 275). The shape selectivity of zeolites in a large number of different reactions (P. B. Venuto, Microporous Materials 2 (1994) 297) is attributed to their microporous channel system having pores in the size of molecules. Although the number of zeolite structures having associated pore sizes increases continuously, accurate tailoring of zeolites is limited by the following facts:

(i) The variation of pore sizes is not continuous but depends upon the available crystal tape and, therefore, can be realized only in an incremental manner.
(ii) Monomodal distributions of the pore sizes comprising pore diameters in the range of 0.8–1.2 nm are unknown.
(iii) The concentration and the incorporation of second elements in the zeolite structure is strongly limited.

While only quite a few elements, such as Ti, Al, P, V, can be isomorphously substituted in the silicate structure, the obtainable concentration will at best be up to 50% and often does not even go beyond 2–3%. Zeolites have already been used as selective heterogeneous catalysts for a great number of organic reactions (P. B. Venuto, Microporous Materials 2 (1994) 297).

We now have found that amorphous microporous mixed metal oxides having an extremely narrow distribution of the microporous and pore diameters in the range of 0.5–1 nm, function as shape selective catalysts in a manner similar to that of the crystalline zeolites. We have found that by using such catalysts t-butyl ether can be directly produced from n-alcohols and t butyl alcohol or isobutene. A formation of t-butyl ether will not be observed under homogeneous conditions. These materials also do faster catalyze the formation of epoxides by direct oxidation of olefins having 6 or less carbon atoms than the formation of epoxides of larger alkenes. The product composition by the hydrogenating crack test of Dean is comparable to the product distribution originating from catalysis with zeolites having large pores such as Y zeolites, zeolite β or SAPO. We have found that such catalytically active amorphous microporous mixed metal oxides can be produced according to a modified sol-gel process. Of special importance for this production is the fact that at least one of the metal components, preferably a Si, Ti, Al or Zr derivative, must be present in a liquid state or in solution, and that the polycondensation in the sol-gel process will not be performed under basic conditions. Thus, no membranes are produced; the produced gel will rather be dried immediately under mild conditions. By rheological examinations we have found that the sol-gel process, catalyzed under acid to neutral reaction conditions, starts with a linear polymerization in such a way that the viscosity in the developing gel being formed increases together with the elasticity. Now, if a gel thus obtained is dried slowly and baked at low heating rates, there will be formed a microporous glass in which the different metal oxides are mixed together on an atomic or almost atomic base, i.e. without a formation of domains of the particular metal oxides. This microporous glass is now ground to the desired grain size and represents the catalyst which is suitable to be used for the shape selective catalysis.

The invention relates to a process for manufacturing shape selective, catalytically active, amorphous, microporous mixed metal oxides by to the sol-gel process, said process being characterized in that at least two hydrolyzable, liquid or dissolved compounds of the elements titanium, silicon, aluminium, zirconium or cerium are dissolved consecutively in one another, the clear solution is agitated at a pH of from 0 to 7 under addition of aqueous acidic catalysts or under addition of fluoride ions to effect a linear polymerization or polycondensation, the obtained gel is gently dried by heating at 60 to 70° C., and is calcinated at temperatures of 120 to 800° C. by using low heating rates whereby a microporous amorphous glass is obtained.

The resulting microporous, amorphous (exhibiting a homogeneous distribution of the elements, i.e. a homogeneous glass—no particles) non-ceramic glasses consist of a matrix of mixed metal oxides, in which at least about 90% of the pores of the material have a diameter between 0.3 and 1.2 nm, of substantially the same pore size and a surface area of more than 50 $m^2/g$.

Preferably, the hydrolyzable liquid or dissolved compounds are selected from the group consisting of $SiO_2$, $TiO_2$, zirconium oxide, cerium oxide, spinel, mullite, silicon carbide, silicon nitride and titanium nitride.

In a further embodiment the matrix of mixed metal oxides contains at least 50% per weight of at least one compound, of the elements titanium, silicon, aluminum, zirconium and cerium, and up to 50% of one or more metal oxides in an atomic distribution selected from the group of the metals of Mo, Sn, Zn, V, Mn, Fe, Co, Ni, As, Pb, Sb, Bi, Ru, Re, Cr, W, Nb, Hf, La, Ce, Gd, Ga, In, Tl, Ag, Cu, Li, K, Na, Be, Mg, Ca, Sr and Ba.

Furthermore, the matrix of mixed metal oxides may additionally contain up to 5% per weight of at least one of the noble metals Pt, Rh, Ir, Os, Ag, Au, Cu, Ni, Pd, Co in highly dispersed form in a metallic or oxidized state.

Acids, particularly hydrochloric acid, are preferred as the acid catalysts.

The calcination temperature is preferably 250 to 500° C.

In a preferred embodiment, the hydrolyzable, soluble compounds are pure alkoxy, mixed alkoxy, alkoxyoxo or acetylacetonate derivatives of the selected metals or metal oxides.

Furthermore, the invention relates to microporous, amorphous, non-ceramic glasses consisting of a matrix of mixed metal oxides, in which at least circa 90% of the pores of the material have a diameter of between 0.3 to 1.2 nm and essentially the same pore size and a surface area of more than 50 $m^2/g$.

Preferably, the matrix of mixed metal oxides consists of at least two of the oxides of titanium, silicon, aluminium, zirconium or cerium.

More particularly, the matrix of mixed metal oxides consists of at least two compounds selected from the group consisting of $SiO_2$, $TiO_2$, $Al_2O_3$, zirconium oxide, cerium oxide, spinel, mullite, silicon carbide, silicon nitride and titanium nitride.

In another embodiment, the matrix of metal oxides consists of at least 50% per weight of one of the compounds of the elements titanium, silicon, aluminum, zirconium or cerium, and up to 50 percent per weight of one or more of metal oxides in an atomic distribution, selected from the group of the metals consisting of of Mo, Sn, Zn, V, Mn, Fe, Co, Ni, As, Pb, Sb, Bi, Ru, Re, Cr, W, Nb, Hf, La, Ce, Gd, Ga, In, Tl, Ag, Cu, Li, K, Na, Be, Mg, Ca, Sr and Ba.

Furthermore, the matrix of mixed metal oxides may additionally contain up to 5% per weight of at least one of the noble elements Pt, Rh, Ir, Os, Ag, Au, Cu, Ni, Pd, Co in a highly dispersed form in a metallic or oxidized state.

The microporous, amorphous, non-ceramic glasses are available by acidic, fluoride catalyzed linear polymerization or polycondensation of hydrolyzable, soluble, compounds mentioned above, preferably of pure alkoxy, mixed alkoxy, alkoxyoxo or acetylacetonate derivatives of the selected metals or metal oxides at a pH of from 0 to 7 in a sol-gel process, followed by mild drying and slow calcination at a final calcination temperature in the range of 120 to 800° C., with the microporous, amorphous, non-ceramic glasses consisting either exclusively of the mixed metal oxides or of the mixed metal oxides and residual surface alkyl or alkoxy groups depending on the selected precursor compound.

The invention also relates to shape selective catalysts consisting of the above defined microporous amorphous, non-ceramic glasses of mixed metal oxides.

Eventually, the invention relates to the use of the microporous, amorphous, non-ceramic glasses of mixed metal oxides or the shape selective catalysts for the catalysis of isomerization reactions, hydrogenation reactions, selective and non-selective oxidation reactions with atmospheric oxygen, hydrogen peroxide or organic peroxides, alkylation reactions, disproportionation reactions, hydrogenation and dehydrogenation reactions, formation of alcohols from olefins, coupling reactions, substitution reactions, cycloaddition reactions or cycloreversion reactions, other formation, cracking of crude oil and hydrocracking, Fischer-Tropsch synthesis of alcohols or hydrocarbons, synthesis of methanol from synthesis gas or methane, for the coating of electrodes in fuel cells or $Li^+$ or other ion storages in batteries, for the formation of membranes for ultrafiltration and gas separation, and for the formation of catalysts with selective cavities for molecular identification.

BRIEF DESCRIPTION OF THE DRAWINGS

The invention will now be described in further detail with reference to the drawings wherein.

Figure 1:
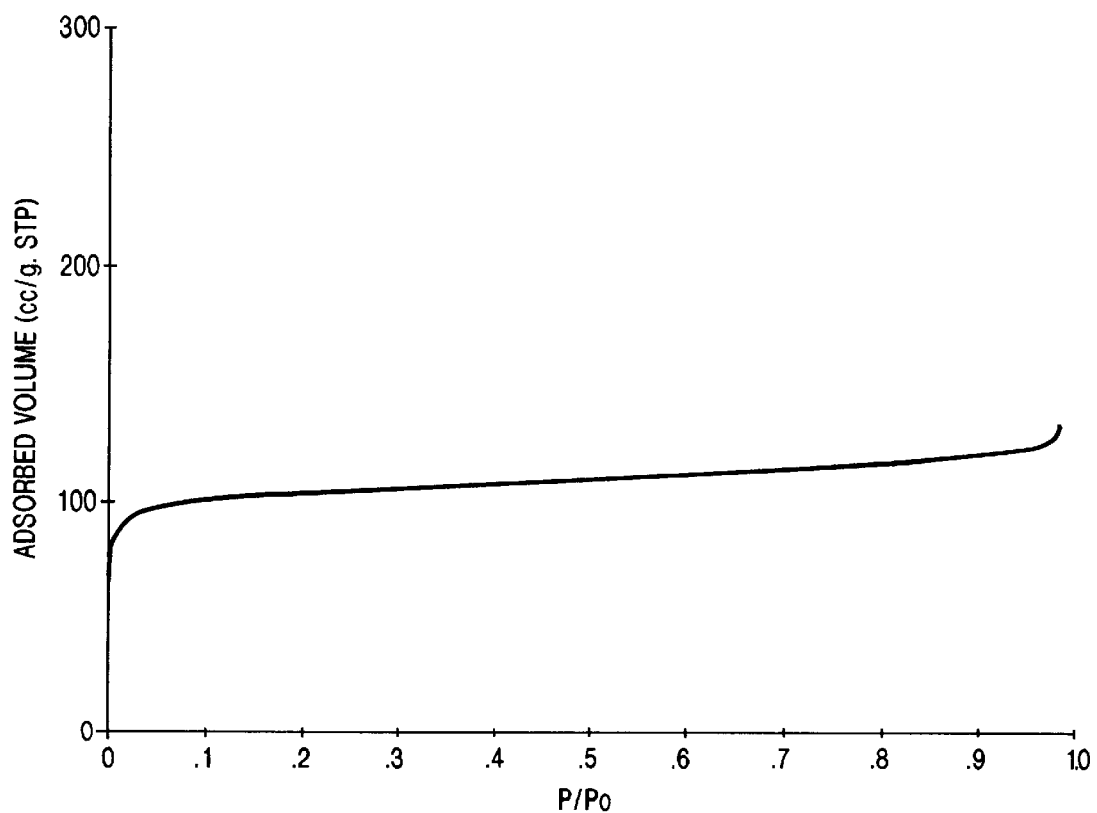
FIG. 1 is a graph depicting a typical $N_2$-adsorption-desorption-isotherm.

The method of preparation of the mixed metal oxides thus obtained is clearly distinguished from that of the preparation of microporous membranes (DE-A-41 17 284), wherein the carrier membrane is pulled out of the sol solution already before the gel point is reached to form a thin continuous film on the carrier membrane, which film will be directly converted into the microporous membrane by means of the described drying and calcination process. The use of the membrane is also basically different from the use of the shape selective catalysts. While the membranes can be used for a molecular separation of gas and liquid mixtures wherein one of the components to be separated will remain, if possible, completely on one side of the membrane and can just scarcely or not at all penetrate the membrane, it is essential for the shape selective catalysis that all reactants will penetrate the pore system of the catalyst and will react in the pores thereof.

The new materials described herein, just like those described above, are distinguished from the microporous membrane catalysts (DE-A-43 03 610) by their mode of preparation. When used, the membrane catalysts are principally different from the shape selective catalysts in that the catalysis with membrane catalysts is based upon the selective preparation of the gaseous and liquid phases in three phase reactions, and improvements over conventional heterogeneous catalysis are due to the selective exclusion by molecular size of undesired reactants or catalyst poison. In membrane catalysis, the properties of the catalyst and the membrane are simultaneously utilized, whereas in the shape selective catalysis all reactants have to be present in the pore system. In contrast to membrane catalysis, the catalysts described herein can be employed directly in the form of powder or molded catalysts by using a conventional reactor technology for the selective catalysis. If membranes are used the selectivity of the catalysis is based upon the exclusion of at least one of the reactants from the pore system of the membrane, whereas the presence of all reactants in the pores is absolutely necessary in the catalysts described herein.

Most highly similar to the materials described herein are the microporous metal oxides (W. F. Maier, T.-C. Tilgner, M. Wiedorn, H.-C. Ko, Advanced Materials 5 (1993) 726). These monometal oxides are different from the materials presented herein above all by the fact that the mixed metal components which are responsible for the catalytic activity are not present as an integral part of the glass matrix. It is novel and hitherto unknown that mixed metal oxides can be prepared in the form of thermally and chemically stable materials which exhibit a narrow distribution of micropores comparable to that of the zeolites as reported herein and which at the same time comprise a homogeneous mixture of the metal oxide components.

The materials presented herein also differ from the catalysts for the selective cavity catalysis (DE-A-43 09 660). While the materials according to the invention described herein are causative for a selective catalysis due to the restricted mobility of the molecules in the interior of the channel structure, the selective catalysis on molecular imprints is based on the molecular recognition of certain structures. Selective cavity catalysts must be tailored for a well-defined structure and are considerably more expensive to prepare than the materials found now. The preparation of the catalyst different, above all, in that in the case of cavity catalysts a polycondensation has to be carried out with the imprint molecule which is anchored to a monomer unit via a chemical bond, which imprint molecule must be removed from the glass before using it as a catalyst. For the newly found catalysts these steps are completely dispensable.

The catalytic activity of amorphous mixed metal oxides is well known. For instance, EP-A-0492 697 describes the preparation of mixed metal oxides from tetraalkyl silicates and a water soluble form of a second metal by means of a basic polycondensation process in the presence of a tetraalkyl ammonium hydroxide. In this polymerization smallest particles are initially formed, and the thus obtained glass, although microporous, shows a significant formation of mesopores which can be attributed to the cavities between the glass particles. Both, the mesopores and the volume of the grain interstices, are not desired if a shape selective catalysis is to be accomplished. We have now found that acid-catalyzed polycondensation of tetraalkyl silicates of up to 50% of a soluble second metal salt can be employed for the preparation of microporous glasses without contamination by mesopores. FIG. 1 shows the typical $N_2$-adsorption-desorption-isotherm in which no indication of a second adsorption due to mesopores can be observed. The isotherm of such a material is identical with the isotherm of crystalline oxides.

Figure 2:
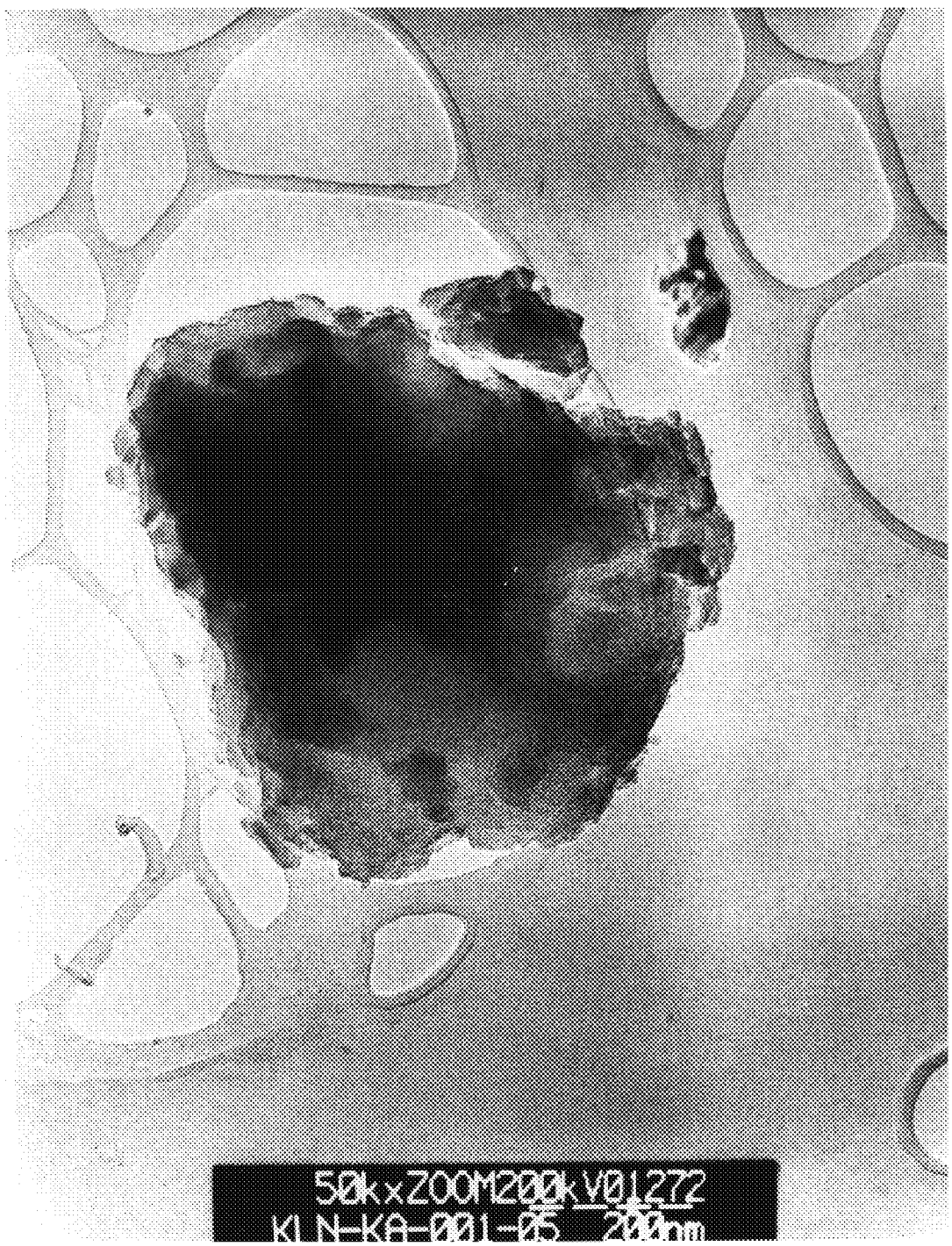
FIG. 2 is a transmission electron micrograph of a material according to the present invention.
Figure 3:
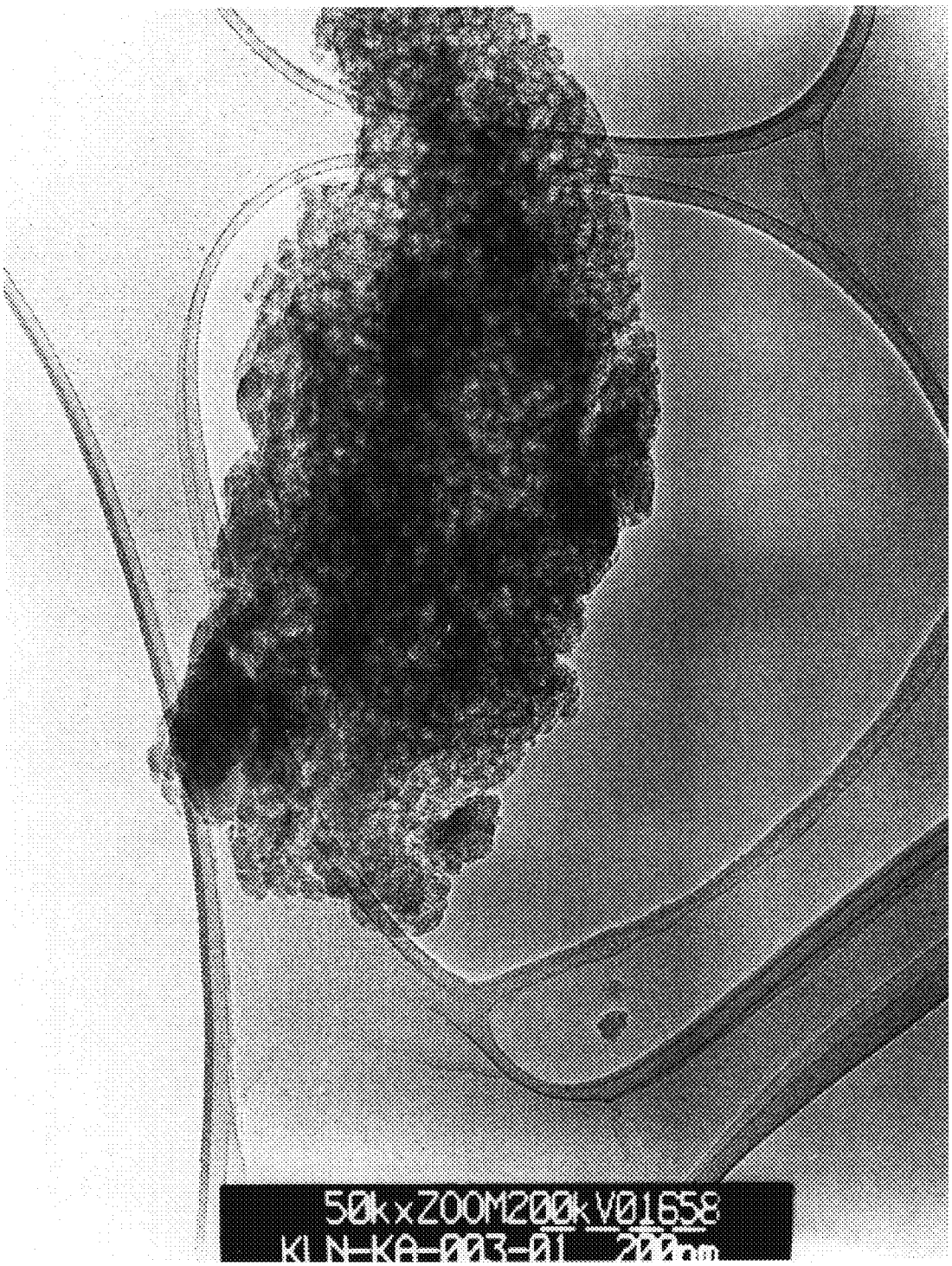
FIG. 3 is a transmission electron micrograph of a material known from EP-A-0 492 697.

The difference between our materials and the materials produced according to EP-A-0 492 697 consists of that our materials can be produced in a pH range of 0 to 7 and in the absence of a template. Our materials show a clean monomodal distribution of the pore sizes in the adsorption and desorption isotherm, whereas a material, produced according to EP A 0 492 697, has a remarkable part of mesoporous neck-of-a-bottle-pores, indicated by the $N_2$-desorption isotherm. Our material still shows the characteristics of a homogeneous glass when using atomic resolution in the transmission electron microscopy (FIG. 2—1272), whereas the material according to EP-A-0 492 697 is composed of fused particles (FIG. 3—1658), indicating that initially the polycondensation is dominated by the known process of particle growth, whereas the formation of the material by linear polymerization is dominant under the conditions according to the invention. When t-butyl either is formed from isobutene in n-hexanol, the known material as described shows only half the activity of our microporous glasses under our standard conditions.

The microporous amorphous mixed metal oxides have large surfaces and porosities comparable to those of zeolites. They can be used for the shape selective catalysis of isomerization reactions, hydrogenation reactions, selective and non-selective oxidation reactions with atmospheric oxygen, hydrogen peroxide or organic peroxides, alkylation reactions, disproportionation reactions, hydrogenation and dehydrogenation reactions, formation of alcohols from olefins, coupling reactions, substitution reactions, cycloaddition reactions or cycloreversion reactions, ether formation, cracking of crude oil and hydrocracking, Fischer Tropsch synthesis of alcohols or hydrocarbons, synthesis of methanol from synthesis gas or methane. They can be used for coating electrodes in fuel cells or $Li^+$ or other ion storages in batteries. They also can be used as ion exchangers or adsorbents. They also are suitable for the formation of membranes for ultrafiltration and gas separation DE-A-41 17 284), for the formation of catalysts with selective cavities for molecular identification (DE-A-43 09 660). The pore size of these microporous glasses can be varied within the range of 0.4–1 nm by changing the alcohol size in polycondensation processes or by changing the drying and calcination processes. The hydrophobicity of the inner surfaces of these materials can be tailored by co-condensation of alkyl metal compounds, preferably alkyl trialkyloxysilanes, during the sol-gel process.

Preparation of the titanium dioxide silicon dioxide glasses with different titanium compounds:

EXAMPLE 1

10 ml of tetraethoxysilane (TEOS), 0.14 ml of $(EtO)_4Ti$ and 8 ml of ethanol are successively dissolved into one another, and 1.6 ml of 8 n HCl are added under stirring. Once the gel formation been completed, the material is heated to 65° C. at a heating rate of 0.5° C./min, is maintained at 65° C. for 3 h, is heated at 250° C. at a heating rate of 0.2° C./min, and is calcinated at this temperature for another 3 h. The adsorption/desorption isotherms show that the material has a true monomodal distribution of the micropores; BET: 471 $m^2/g$; pore diameter: 0.67 nm.

EXAMPLE 2

Other titanium tetraalcoholates are usable. 46.3-x mmoles of TEOS, x mmoles of $(iPrO)_4Ti$, wherein x can be 0 to 43.3, and 140 mmoles of ethanol are successively dissolved into one another, and 2 ml of 8 n HCl are added under stirring. The mixture is maintained at room temperature within a period of 3 days. Once the gel formation has been completed, the material is heated to 65° C. at a heating rate of 0.5° C./min, is maintained at 65° C. for 3 h, is heated to 250° C. at a heating rate of 0.2° C./min, and is calcinated at this temperature for another 3 h. The adsorption/desorption isotherms show that the material has a true monomodal distribution of the micropores; BET: 180 (60% Ti) to 600 (3% Ti) $m^2/g$; pore diameter: 0.73–0.8 nm.

EXAMPLE 3

Vanadium Oxide-silicon Dioxide Glass 10 ml of tetraethoxysilane (TEOS), 1,2 g of vanadyl acetylacetonate $(O=V)AcAc)_2$) and 8 ml of ethanol are successively dissolved into one another, and 2 ml of 8 n HCl are added under stirring. Once the gel formation has been completed, the material is heated to 65° C. at a heating rate of 0.5° C./min, is maintained at 65° C. for 3 h, is heated to 250° C. at a heating rate of 0.2° C./min, and is calcinated at this temperature for another 3 h. The adsorption/desorption isotherms show that the material has a true monomodal distribution of the micropores; BET: 542 $m^2/g$; pore diameter: 0.66 nm.

EXAMPLE 4

Zirconium Dioxide-silicon Dioxide Glass 10 ml of tetraethoxysilane (TEOS), 1 ml of $(BuO)_4Zr$ and 8.4 ml of ethanol are successively dissolved into one another, and 2 ml of 2 n HCl are added under stirring. Once the gel formation been completed, the material is heated to 65° C. at a heating rate of 0.5° C./min, is maintained at 65° C. for 3 h, is heated at 250° C. at a heating rate of 0.2° C./min, and is calcinated at this temperature for another 3 h. The adsorption/desorption isotherms show that the material has a true monomodal distribution of the micropores; BET: 240 $m^2/g$; pore diameter: 0.65 nm.

EXAMPLE 5

Aluminum Oxide Silicon Dioxide Glass 27.5 ml of $(EtO)_4Si$, 0.45 ml of triisobutylaluminium, 2.01 ml of tetra-n-propoxy zirconium and 25 ml ethanol are successively dissolved into one another, and 4.5 ml of 0.4 n HCl are added under stirring for 10 minutes. Thereby, the temperature is raised up to 60° C. After the completion of the gel formation and after a slow pre-drying at room temperature, the material is heated to 65° C. at a heating rate of 0.5° C./min, is maintained at 65° C. for 3 hr, is heated to 300° C. at a heating rate of 0.2° C./min, and is calcinated at this temperature for another 3 h. The adsorption/desorption isotherms show that the material has a true monomodal distribution of the micropores; BET: 280 m²/g; pore diameter: 0.7 nm.

EXAMPLE 6

Titanium Dioxide-zirconium Dioxide-silicon Dioxide Glass 10 ml of tetraethoxysilane (TEOS), 1 ml of (BuO)$_4$Ar and 8 ml of ethanol are successively dissolved into one another, and 2 ml of 8 n HCl are added under stirring. Once the gel formation been completed, the material is heated to 65° C. at a heating rate of 0.5° C./min, is maintained during at 65° C. for 3 h, heated at 250° C. at a heating rate of 0.2° C./min, and is calcinated for another 3 h at this temperature. The adsorption/desorption isotherms show that the material has a true monomodal distribution of the micropores; BET: 520 m²/g; pore diameter: 0.75 nm.

EXAMPLE 7

Shape Selectivity of the Epoxidation of Alkenes 15.8 mmoles of alkene, 1 ml of a 3 n solution of t-butyl hydroperoxide and 50 mg of titanium oxide-silicon dioxide glass are stirred during 15 min at 80° C., and the composition of the product is analyzed by gas chromatography. The relative transformation of the individual alkenes into epoxides, in comparison to the slowest reaction=1, is indicated in rackets: 1-hexene (9), 1-heptene (3), 1-octene (4), 1-nonene (3), 1-denene (3), 1-dodecene (2), 1-pentadecene (1), and cyclohexene (9), cycloheptene (2), cyclooctene (1), and cyclodecene (1). Since the various terminal alkenes and the various cycloalkenes possess about the same reactivity under the homogeneous conditions of the epoxide formation, the results indicate a strong preference of the formation of epoxides of the smaller alkenes, which indicates a molecular shape selectivity caused by monomodal micropores of the glass.

EXAMPLE 8

Shape Selectivity in Favor of the Formation of t-butyl Ether 300 mmoles of i-butene, 100 mmoles of 1-hexanol and 2.5 g of Ti-Si-catalyst powder are stirred in a 100 ml autoclave at a pressure of 40 bar N$_2$ and a temperature of 150° C. over a period of 18 h. 62% of n-hexanol were converted into hexyl-t-butyl ether with a selectivity of 92%.

EXAMPLE 9

Shape Selectivity in Favor of the Formation of t-butyl Ether 300 mmoles of i-butene, 100 mmoles of 1-hexanol and 2.5 g of Ti-Si-catalyst powder are stirred in a 100 ml autoclave at a pressure of 40 bar N$_2$ and a temperature of 150° C. over a period of 17 h. 17% of n-hexanol were converted into hexyl t-butyl ether with a selectivity of 90%.

EXAMPLE 10

Shape Selectivity in the Hydrocracking of n-decane

A microporous amorphous glass of mixed Ti—Si oxides was impregnated with 1% of Pt and was subjected to the standardized hydrocracking test as described in the literature (J. A. Martens, M. Thielen, P. A. Jacobs, J. Weitkamp, Zeolites 4 (1984) 98–107). The microporous Ti—Si glass showed a Constraint Index (CI*) of 1.5, a EC8 (% of ethyloctane) of 10.3, a PC7 (% of 4-propylheptane) of 0.9, a DB iC10 (% of double-branched C10 isomers) of 30, a iC5 (isopentane in the cracked product) of 30.5, and a Pore Dimension Index of 14.9. The CI* can be used for the estimation of the pore size, and shows that the pores are larger than in ZSM12 zeolites and smaller than in Y-zeolites. EC8 confirms that the Broensted acidic centers are localized in the pores, and that the material behaves like a SAPO-5-zeolite. PC7 shows that the pores are similar to those of a FAU-zeolite. The DBiC10 is similar to that of SAPO-5 indicating a similar pore system. The iC5 confirms that the glass belongs to the group of large-pored zeolites. The DI indicates the absence of connected pores. In total, the hydrocracking test of decane shows that the Broensted acidic centers of the glass are localized in a shape selective environment. The micropores of the glass have a tubular shape with a pore diameter of 0.7 0.8 nm.

EXAMPLE 11

Preparation of a Mixed Oxides Catalyst Comprising 2 Mole-% of In in Si 0.471 g of indium nitrate are dissolved in a 50 ml PP-beaker in 14 ml of ethanol under stirring. After slow addition of 20 ml of TEOS, 3.49 ml of 8N HCl were added dropwise. Then stirring the clear solution was continued over a period of several days until gelation occurred. The transparent glass was broken into smaller pieces, and it was calcinated in air at 250° C. over a period of 10 h (heating-up rate: 2.5° C./min). After the calcination had been completed, the catalyst particles were ground to a particle size of <200 μm.

EXAMPLE 12

Selective Oxidation of Propene with Air to Form 1, 5-hexadiene 50 mg of the mixed oxides catalyst comprising 2 mole % of In in Si (Example 11) were tightly packed in the center of a quartz tube of a vapor phase flow reactor (length: 30 cm, inner diameter: 4 mm) and heated to the reaction temperature of 590° C., while the gas mixture, consisting of 90 vol.-% propene and 10% air (flow rate (propene)=37.8 ml/min; (air)=4.2 ml/min), was allowed to continuously flowing through the catalyst bed. After a stationary state had been reached, the product gas mixture was frozen out in a cold trap at 78° C. and analyzed by gas chromatography. A selectivity of 1,5-hexadiene of 95% was obtained at a propene conversion of of 5–10%.

EXAMPLE 13

Preparation of a Mixed Oxides Catalyst Comprising 6 Mole-% Cu in Si 1.313 g of copper(II)diacetylacetonate (Cu(acac)$_2$) were dissolved in 14.6 ml ethanol in a 50 ml-PP beaker under stirring. After slow addition of 20 ml TEOS, 3.63 ml 8 n HCl were added dropwise. Then stirring of the clear solution was continued over a period of several days until gelation occurred. The transparent glass was broken into smaller pieces, and it was calcinated in air at 250° C. over a period of 10 h (heating-up rate: 2.5° C./min). After the calcination being completed, the catalyst particles were ground to a particle size of <200 μm.

EXAMPLE 14

Selective Oxidation of Propene with Air to Form Acroleine 50 mg of the mixed oxides catalyst comprising 6% Cu-in-Si (Example 13) were tightly packed in the center of the quartz tube of the reactor (the reactor is identical to that used in Example 12) and heated to the reaction temperature of 370° C. while the gas mixture, consisting of 28.6 vol.-% propene and 71.4% air (flow rate (propene)=25 ml/min; (air)—62.5 ml/min), was allowed to continuously flow through the catalyst bed. After a stationary state had been reached, the product gas mixture was frozen out in a cold trap at −78° C. and analyzed by gas chromatography. A selectivity of acroleine of 85% was obtained at a propene conversion of of 4–8%.

What is claimed is:

1. A microporous, amorphous, non-ceramic glass, which consists of a matrix of mixed metal oxides, wherein the matrix comprises micropores, at least about 90% of said micropores are of substantially equal size, and said size is a diameter between 0.3 and 1.2 nm, and wherein the matrix has a surface area of more than 50 $m^2/g$.

2. The microporous, amorphous, non-ceramic glass according to claim 1 wherein the matrix of mixed metal oxides consists of at least two compounds selected from the group consisting of oxides of titanium, silicon, aluminum, zirconium and cerium.

3. The microporous, amorphous, non-ceramic glass according to claim 1, wherein the matrix of mixed metal oxides consists of at least two compounds selected from the group consisting of $SiO_2$, $TiO_2$, zirconium oxide, corium oxide, spinel, mullite, silicon carbide, silicon nitride and titanium nitride.

4. The microporous, amorphous, non-ceramic glass according to claim 1, wherein the matrix of mixed metal oxides consists of at least 50% by weight of a metal oxide selected from the group consisting of oxides of titanium, silicon, aluminum, zirconium and cerium, and up to 50% per weight of one or more metal oxides in an atomic distribution selected from the group of metals consisting of Mo, Sn, Zn, V, Mn, Fr, Co, Ni, As, Pb, Sb, Bi, Ru, Re, Cr, W, Nb, Hf, La, Ce, Gd, Ga, In, Tl, Ag, Cu, Li, K, Na, Be, Mg, Ca, Sr and Ba.

5. The microporous, amorphous, non-ceramic glass according to claim 1, additionally containing up to 5% by weight of at least one of the noble metals Pt, Rh, Ir, Os, Ag, Au, Cu, Ni, Pd, Co in a highly dispersed form in a metallic or oxidized stage.

6. The microporous, amorphous, non-ceramic glass according to any one of claims 1 or 2–5, which is obtained by a process comprising:

a) acid or fluoride catalyzed linear polymerization or polycondensation of at least two hydrolyzable, liquid or dissolved compounds comprising metals selected from the group consisting of titanium, silicon, aluminum, zirconium and cerium at a pH of 0 to 7 in a sol-gel process; and followed by b) drying of the product of a) at a temperature of 60 to 70° C. and calcination of the product of a) at a temperature of 120 to 800° C.

7. The microporous, amorphous, non-ceramic glass according to claim 6, which is obtained by a process comprising:

a) acid or fluoride catalyzed linear polymerization or polycondensation of at least two hydrolyzable, liquid or dissolved compounds selected from the group consisting of pure alkoxy, mixed alkoxy, alkoxyoxo or acetylacetonate derivatives comprising metals selected from the group consisting of titanium, silicon, aluminum, zirconium and cerium at a pH of 0 to 7 in a sol-gel process; followed by b) drying of the product of a) at a temperature of 60 to 70° C. and calcination of the product of a) at a temperature of 120 to 800° C.

8. A shape selective catalyst consisting of a microporous, amorphous, non-ceramic glass according to claim 6.

9. A shape selective catalyst consisting of a microporous, amorphous, non-ceramic glass according to any one of the claims 1, 2–5, or 7.

* * * * *